(12) United States Patent
Murali et al.

(10) Patent No.: US 9,726,687 B2
(45) Date of Patent: Aug. 8, 2017

(54) SYSTEM AND METHOD FOR PROCESSING OF BIOLOGICAL TISSUE SAMPLES

(71) Applicant: STEMPEUTICS RESEARCH PRIVATE LIMITED, Bangalore (IN)

(72) Inventors: Cherat Murali, Bangalore (IN); Damle Alok, Bangalore (IN); Sundar Raj Swathi, Bangalore (IN); Majumdar Anish Sen, Bangalore (IN); Deshmukh Abhijeet, Bangalore (IN); Sathya Kumar Byalappa Manjunath, Bangalore (IN); Lohidhakshan Prajod Thiruvampattil, Bangalore (IN)

(73) Assignee: STEMPEUTICS RESEARCH PRIVATE LIMITED, Bangalore, Karnataka (IN)

( * ) Notice: Subject to any disclaimer, the term of this patent is extended or adjusted under 35 U.S.C. 154(b) by 15 days.

(21) Appl. No.: 15/032,845

(22) PCT Filed: Nov. 12, 2014

(86) PCT No.: PCT/IB2014/065975
§ 371 (c)(1),
(2) Date: Apr. 28, 2016

(87) PCT Pub. No.: WO2015/071829
PCT Pub. Date: May 21, 2015

(65) Prior Publication Data
US 2016/0252537 A1 Sep. 1, 2016

(30) Foreign Application Priority Data
Nov. 13, 2013 (IN) .......................... 5151/CHE/2013

(51) Int. Cl.
G01N 35/00 (2006.01)
G01N 35/02 (2006.01)
(Continued)

(52) U.S. Cl.
CPC ......... *G01N 35/0099* (2013.01); *C12M 41/48* (2013.01); *C12M 45/02* (2013.01);
(Continued)

(58) Field of Classification Search
CPC .................................................... G01N 35/00
See application file for complete search history.

(56) References Cited

U.S. PATENT DOCUMENTS

2003/0092186 A1* 5/2003 Pressman ............... B01D 61/18
436/46
2008/0014181 A1 1/2008 Ariff et al.

FOREIGN PATENT DOCUMENTS

WO WO2004/073846 9/2004
WO WO2005/012480 2/2005
(Continued)

OTHER PUBLICATIONS

International Search Report and Written Opinion for PCT/IB2014/065975, issued Feb. 17, 2015,10 pages.
(Continued)

*Primary Examiner* — Sean E Conley
*Assistant Examiner* — Benjamin R Whatley
(74) *Attorney, Agent, or Firm* — Foley & Lardner LLP

(57) ABSTRACT

The present disclosure provides an automated system for processing of tissue. The system comprises a plurality of containers for storing at least one of tissue samples, buffer solutions, enzymes and other reagents, tissue processing container for processing of the tissue, and a robotic assembly coupled to the tissue processing container. The robotic assembly is configured to: carry the tissue processing container towards each of the plurality of containers, and align an inlet port of the tissue processing container with an outlet port of each of the plurality of containers for collecting the liquids, and moves the tissue processing container in mul-
(Continued)

tiple-planes to perform at least one of the washing processes, digestion process, phase separation process and combination thereof. The system also comprises of a control unit interfaced with the robotic assembly for controlling operations of the robotic assembly while processing the tissue.

20 Claims, 11 Drawing Sheets

(51) Int. Cl.
  *C12M 1/33*  (2006.01)
  *C12M 1/00*  (2006.01)
  *C12N 5/071* (2010.01)
  *C12M 1/36*  (2006.01)
(52) U.S. Cl.
  CPC ............ *C12M 45/09* (2013.01); *C12M 47/04* (2013.01); *C12N 5/069* (2013.01); *G01N 35/02* (2013.01); *G01N 2035/00346* (2013.01); *G01N 2035/00891* (2013.01)

(56) References Cited

FOREIGN PATENT DOCUMENTS

| WO | WO2008/018904 | 2/2008 |
| WO | WO2013/030761 | 3/2013 |

OTHER PUBLICATIONS

Wathi Sundarraj, Nancy Priya, Abhijeet Deshmukh, Murali Cherat and Anish Sen Majumdar: "Development of an Automated Device for Point-Of-Care Isolation of Stromal Vascular Fraction Cells from Adipose Tissue Lipoaspirate", IPRAS Journal, Jul. 1, 2013 (Jul. 1, 2013), pp. 43-44, XP055167879.

Yoshimura, K. et al., "Cell-Assisted Lipotransfer for Cosmetic Breast Augmentation: Supportive Use of Adipose-Derived Stem/Stromal Cells," Aesth Plast Surg (2008), 32:48-55.

Gimble et al., Clinical and Preclinical Translation of Cell-based Therapies Using Adipose Tissue-Derived Cells, stem cell research & therapy 2010, 1:19, http://\stemcellres.com/content/1/2/19, 8 pages.

\* cited by examiner

SYSTEM AND METHOD FOR PROCESSING OF BIOLOGICAL TISSUE SAMPLES

CROSS-REFERENCE TO RELATED APPLICATIONS

The present application is a U.S. national stage application claiming the benefit of International Application No. PCT/IB2014/065975, filed on Nov. 12, 2014, which claims priority from Indian Patent Application No. 5151/CHE/2013 filed Nov. 13, 2013, the entire contents of which are incorporated herein by reference in their entirety.

TECHNICAL FIELD

The present disclosure relates to a system and method for processing of biological tissue samples, more particularly embodiments relate to an automated system and method for processing of tissue to isolate cells.

BACKGROUND AND PRIOR ART

Mesenchymal stem/stromal cells (MSC) can be isolated from several adult tissues such as bone marrow, adipose, placenta and umbilical cord among others, and are highly promising sources for regenerative medicine. While bone marrow is the most conventional source of MSC, the major limitation in its clinical application is that the concentration of MSC in bone marrow is very low. Subcutaneous adipose tissue is a promising alternative source as it has a high content of MSC, and can be easily obtained by methods such as liposuction or lipectomy.

Adipose tissue can be enzymatically disrupted to yield two main cell populations: mature adipocytes and the stromal vascular fraction (SVF). The SVF is a heterogeneous cell mixture comprising of preadipocytes, mature endothelial cells (EC), endothelial progenitor cells (EPC), vascular smooth muscle cells (SMC), pericytes, mural cells, macrophages, fibroblasts and adipose-derived stem/stromal cells (ASC). The ASC are self-renewing multipotent mesenchymal progenitors that can be easily differentiated into adipocytes, osteoblasts and chondrocytes. Additionally, several investigators have also derived endothelial, myogenic, hepatic and neuronal lineages from ASC under specific inductive conditions. In addition to their plasticity, ASC also secrete bioactive molecules such as immunomodulators and trophic, antiapoptotic, antiscarring, angiogenic, and mitotic factors. Thus, the SVF and ASC from fat tissue have enormous potential in cell-based therapy.

Non-expanded SVF cells are particularly well-suited for autologous cell therapy where clinical doses of the patient's own fat-derived stem cells can be transplanted back with minimal manipulation. SVF cells have been shown to have therapeutic benefit in several preclinical disease models, as well as in clinical trials for indications such as Crohn's disease, graft-versus-host disease, autoimmune and allergic pathologies like multiple sclerosis and inflammatory bowel disease, myocardial infarction, limb ischemia, non-healing chronic wounds, radiation injury, urinary incontinence etc. (Gimble et al. *Stem Cell Research & Therapy* 2010). They also have huge potential in cosmetic and reconstructive medicine as they have been shown to prolong survival of autologous fat grafts. A clinical study conducted by Yoshimura et. al. (Yoshimura et. al. *Aesth Plast Surg,* 2008) has demonstrated efficacy of SVF enrichment in fat grafting for breast augmentation. Fat grafting can be applied for post-surgical breast reconstruction, cosmetic breast augmentation, restructuring of facial folds, wrinkle correction and many other soft-tissue defects. Studies in animal models have shown that enrichment of fat grafts with SVF cells promotes engraftment by improving vascularization of the graft, as well as by enhancing turnover of adipocytes, and secretion of anti-apoptotic factors. In fact, the heterogenous composition of the SVF, particularly the high content of endothelial progenitor cells, is ideal for pro-angiogenic cell therapy and vascular repair. Several groups have identified CD34 positive cells in the SVF, capable of stimulating angiogenesis directly or through the release of growth factors such as IGF-1, HGF and VEGF; and SVF cells have been shown to have neo-vasculogenic potential in animal models.

Conventional procedures for isolation of SVF involve manual processing by enzymatic digestion of the lipoaspirate tissue with collagenase, which breaks down the stromal matrix to release the SVF cells. The SVF is then separated from the fat fraction by centrifugation. The conventional manual procedure of isolation has several limitations in the context of clinical application:

Firstly, the fat tissue needs to be transported from the hospital to a GMP-compliant laboratory, wherein storage, handling and transportation of the fat tissue can affect the yield, viability and quality of cells contained in SVF. Further, the time taken for transportation, isolation and delivery of cells is very long.

Secondly, the patient has to undergo more than one sitting at the point of care, and cannot be used in conditions of emergency where the cells are required immediately (eg: for wound healing, burns, myocardial infarction etc.). Further, bench-top open system processing requires rigorous quality control of the therapeutic product.

A few approaches to develop an automated, closed device/system for processing stem cells are already in place. One such automated system for processing of biological samples is disclosed in the PCT publication number WO2005012480 hereinafter referred as '480 publication. The automated system of the '480 publication includes one or more of a collection chamber, a processing chamber, a waste chamber, an output chamber and a sample chamber. The various chambers are coupled together via one or more conduits such that fluids containing biological material may pass from one chamber to another in a closed, sterile fluid/tissue pathway. In certain embodiments, the waste chamber, the output chamber and the sample chamber are optional. The system also includes a plurality of filters. The filters are effective to separate the stem cells and/or progenitor cells from, among other things, collagen, adipocytes, and tissue disaggregation agents that may be present in the solution in connection with the processing of adipose tissue.

Another such automated system for processing of biological samples is disclosed in US Patent publication no. US 20080014181 herein after referred as '181 publication. The automated system of '181 publication apparatus can be used in combination with complementary devices such as cell collection device and/or a sodding apparatus to support various therapies. The automated apparatus of '181 publication includes a cell separation apparatus having a media reservoir. A cell processing device is provided in the cell separation apparatus, wherein the cell processing device comprises at least one inlet and at least one outlet, a first lobe and a second lobe. Further, the cell separation apparatus comprises at least one pump, and at least one valve adapted to divert or prevent fluid flow.

The automated devices disclosed in the prior art documents employs fluid supply mediums such as tubes, hoses for supplying the liquids in between storage containers and the processing container. The fluid supply mediums are to be connected manually before starting the process, which can contribute to errors. Manual connection is also a risk factor that can compromise the sterility or aseptic nature of the cell isolation system. Improper handling can introduce microbial contamination or a breach in the closed nature of the cell isolation system. In addition, to supply the fluid through fluid mediums, pumps are used. The pumps draw the fluid from the storage containers, and supply it to the cell concentration chamber, thereby impart pressure onto the liquid. It is known that the tissues used for extracting cells should not be subjected to pressure, since it will affect the cells in the tissue and thereby reduces the yield of viable cells. Hence there is a need to develop a system for processing biological tissues in aseptic conditions without use of tubes and pumps.

In light of foregoing discussion, it is necessary to develop an improved automated system for processing of biological tissue samples to overcome the problems stated above.

SUMMARY OF THE DISCLOSURE

Embodiments of the present disclosure provide automated systems which can operate in multiple planes and perform multiple functions having additional advantages are provided through the provision of a system as claimed in the present disclosure.

Additional features and advantages are realized through the techniques of the present disclosure. Other embodiments and aspects of the disclosure are described in detail herein and are considered a part of the claimed disclosure.

In one non-limiting embodiment of the present disclosure there is provided an automated tubeless system for processing of tissue to isolate cells. The system comprises a plurality of containers, wherein each of the plurality of containers stores at least one of tissue samples, buffer solutions, enzymes and reagents. A tissue processing container for processing of the tissue, and a robotic assembly coupled to the tissue processing container for carrying the tissue processing container for processing the tissue. The robotic assembly is configured to: carry the tissue processing container towards each of the plurality of containers, and align an inlet port of the tissue processing container with an outlet port of each of the plurality of containers for collecting at least one of tissue samples, buffer solutions, enzymes and reagents; move the tissue processing container in multiple-planes to perform at least one of the washing processes, digestion process, phase separation process and combination thereof for separating an aqueous fraction and a fatty fraction from the digested tissue samples. The system also comprises a control unit interfaced with the robotic assembly for controlling operations of the robotic assembly while processing the tissue.

In an embodiment of the disclosure, the tissues are mammalian tissues selected from at least one of adipose tissue, placental tissue, bone-marrow tissue and umbilical cord tissue. In an exemplary embodiment, the system is used for isolating Stromal Vascular Fraction (SVF) cells by processing the adipose tissue, and multi-potent stem/stromal cells from placental and umbilical cord tissue.

In an embodiment of the disclosure the system comprises a cell concentration unit configured to filter the aqueous fraction of digested tissue for isolating the component cells, wherein the cell concentration unit receives the aqueous fraction sample from the tissue processing container. The cell concentration unit is at least one of filter assembly, spinner and a centrifugation assembly.

In an embodiment of the disclosure the system is optionally enclosed in a chamber.

In an embodiment of the disclosure, the control unit is provided with a user interface having a display unit and input buttons to feed in required parameters for processing the tissue.

In an embodiment of the disclosure the system comprises at least one temperature sensor, placed in a chamber to measure and regulate the temperature of the chamber, wherein the temperature sensor is interfaced with the control unit. Further, at least one heating element is placed in a chamber, wherein the heating element is interfaced with the control unit to maintain the temperature of the chamber within a predetermined range of temperature, and heat the contents of the tissue processing container. Additional heating modules, temperature sensors and controllers can be used to control the ambient temperature inside the system.

In an embodiment of the disclosure, the outlet port of each of the plurality of containers and the inlet port of the tissue processing container are provided with a valve assembly. The valve assemblies are interfaced with the control unit.

In an embodiment of the disclosure the system comprises a wash container adapted to be anchored and operated by the robotic assembly. The robotic assembly is configured to: Carry the wash container towards the plurality of containers, and align an inlet port of the wash container with an outlet port of a container which is storing the wash buffer solution for collecting the wash buffer solution; and carry the wash container towards a cell concentration unit, and align the outlet port of the wash container with an inlet port of the cell concentration unit for supplying the wash buffer solution to the cell concentration unit for washing the aqueous fraction tissue sample.

In an embodiment of the disclosure, each of the plurality of containers and the tissue processing container are equipped with radio frequency identification tags.

In an embodiment of the disclosure, the robotic assembly comprises a plurality of sensors. The plurality of sensors are interfaced with the control unit to control the movement of the robotic assembly in a predefined path.

In another non-limiting embodiment of the disclosure there is provided a method for processing of tissue using the automated system. The method comprises acts of: receiving tissue samples and wash buffer solution to a tissue processing container wherein the robotic assembly aligns inlet ports of the tissue processing container to outlet ports of the containers storing tissues and wash buffer solution. Then, washing the tissue samples with wash buffer solution by agitating the mixture in the tissue processing container with the help of robotic assembly, wherein the robotic assembly moves the tissue processing container in multiple planes, allowing phase separation of the mixture to obtain an initial fatty upper fraction and an initial aqueous lower fraction in the tissue processing container, wherein the phase separation is carried out by tilting the tissue processing container by 90 degrees with respect to X axis by a robotic assembly, and disposing the initial lower aqueous fraction obtained in step (c) to a waste collection unit, wherein the robotic assembly aligns inlet ports of waste collection unit with an outlet port of the tissue processing container. Then, receiving a predetermined quantity of a digestive buffer contained in a digestive buffer container to the tissue processing container, wherein the robotic assembly aligns inlet ports of the tissue processing container to outlet ports of the container storing digestive buffer solution. Digesting the fatty upper fraction with the digestive buffer by agitating the mixture in the tissue processing container with the help of robotic assembly, wherein the robotic assembly moves the tissue processing container in multiple planes, and allowing phase separation of the mixture in the tissue processing container to obtain a final fatty upper fraction and a final aqueous lower fraction, wherein the phase separation is carried out by tilting the tissue processing container by 90 degrees with respect to X axis by a robotic assembly.

In an embodiment of the disclosure the method comprises act of detecting position of the robotic assembly by sensors, and regulating the robotic unit by the control unit to carry the tissue processing container toward each of the plurality of containers and the waste collection unit.

In an embodiment of the disclosure the method comprises act of detecting the alignment of tissue processing container with at least one of the plurality of containers and waste collection unit by a control unit, and operating the valve assembly.

It is to be understood that the aspects and embodiments of the disclosure described above may be used in any combination with each other. Several of the aspects and embodiments may be combined together to form a further embodiment of the disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING FIGURES

The novel features and characteristics of the disclosure are set forth in the appended description. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which.

Figure 1A:
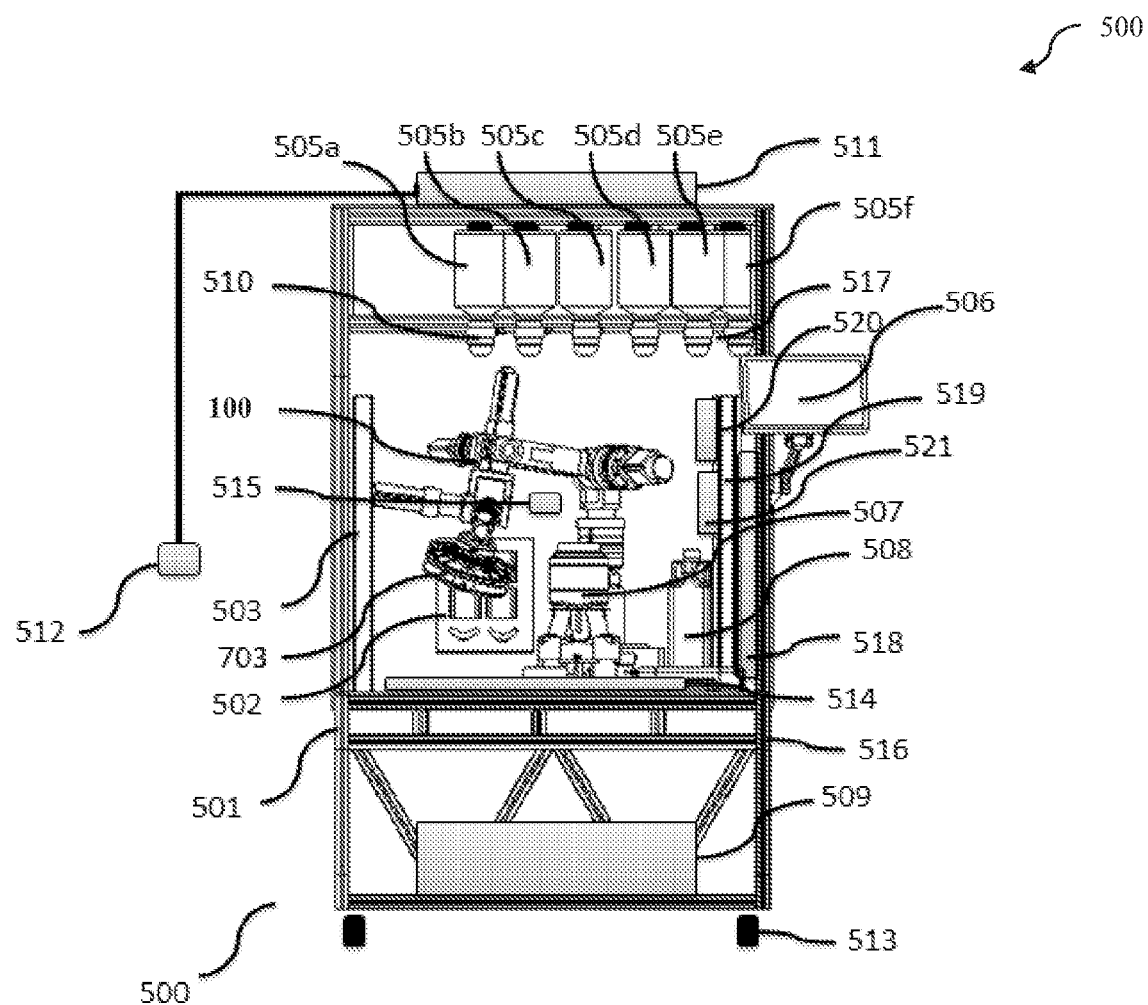
FIGS. 1a and 1b illustrates a front view and perspective views of an automated system for isolating cells from tissue.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

To overcome the drawbacks mentioned in the background, the present disclosure provides a point-of-care tubeless system for isolation of clinical grade cells such as but not limiting to Stromal Vascular Fraction (SVF) from tissue such as lipoaspirated fat tissue. Accordingly, the present disclosure discloses an automated bench-top/table-top or portable point-of-care aseptic system for processing adipose tissue to isolate SVF, and is programmed to be operated by a user machine interface guiding the user.

The system as disclosed in the present disclosure is a closed, automated, point-of-care, bench-top or trolley mounted or fixed tubeless system facilitated with a robotic mechanism for isolation of clinical grade stromal vascular fraction (SVF) from adipose tissue, and a method for isolation of stromal vascular fraction (SVF) from adipose tissue sample by employing the system. A point-of-care system would ensure that the processing and delivery of the final cell product consumes minimal time, and the cells are delivered to the patient in a single sitting, within a couple of hours of the fat aspiration procedure in a clinic/hospital setting. The system is further provided with means to optionally remove red blood cells. The automation of the procedure eliminates the need for specialized personnel with Good Manufacturing Practice (GMP) experience, and maintains consistency of the end product. The entire isolation procedure would be carried out in a closed automated system facilitated with a robotic mechanism with clinical grade sterile disposable components.

This automated system broadly comprises of two modules: Module 1 comprises a tissue processing container and robotics assembly—wherein the tissue sample is washed and is subjected to enzymatic digestion. Whereas the Module 2 is a cell concentration unit for obtaining concentrated cells, for example SVF, through filtration or centrifugation. The filtration can be performed by techniques such as but not limiting to simple filtration, pressure assisted filtration, vacuum assisted filtration, and vibration assisted filtration or any combination thereof. Further, the centrifugation process can be carried out by any centrifugation process which is known in the art. The system further is automated, which includes robotic mechanism, electronic components, and computerized control system for mammalian tissue digestion, heating, wash, separation and concentration of cells under aseptic conditions in a hospital or clinical setting.

The present disclosure also discloses a method for processing of tissues for obtaining cells from tissues, for example, stromal vascular fraction (SVF) cells from adipose tissue using the system explained above. The method comprises acts of transferring a predetermined quantity of a tissue sample followed by a wash buffer solution from the storage containers into a tissue processing container, by connecting storage containers to the valve system of the tissue processing container using robotic assembly. In an optional embodiment of the disclosure, the tissue is supplied to a tissue processing container by connecting a tube between the tissue processing container and a tissue harvest canister. Then washing the tissue samples with wash buffer solution; agitating the mixture in the tissue processing container with the help of robotic assembly, to allow phase separation of the mixture to obtain an initial fatty upper fraction and an initial aqueous lower fraction in the tissue processing container. In an embodiment of the disclosure, the phase separation step referred herein above and below is carried out while processing of adipose tissue. The initial lower aqueous fraction obtained from the previous step is disposed to a waste collection unit by carrying the tissue processing container towards the waste collection unit using the robotic assembly, and connecting the same through a valve system. Then, transferring a predetermined quantity of a digestive buffer from storage container to the tissue processing container by connecting the tissue processing container to the storage container by movement of the robotic assembly. After transfer of digestive buffer, the tissue processing container is agitated along a predetermined path for a predetermined time by the robotic arm movement, for digesting the initial fat fraction with the digestive buffer. Now, allowing phase separation of the mixture in the tissue processing container by the help of robotic assembly to obtain a final fatty upper fraction and a final aqueous lower fraction. Then, the final aqueous lower fraction containing the SVF cells is transferred to a cell concentration unit by the movement of robotic assembly. The final aqueous fraction is supplied to the cell concentration unit for concentrating the cells using filtration assembly of the cell concentration unit, optionally along with removal of red blood cells to obtain said SVF cells. All the components in the system which comes into contact with the tissue are designed in such a way to be of single use disposables.

The terms "comprises", "comprising", or any other variations thereof, are intended to cover a non-exclusive inclusion, such that a setup system, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

Reference will now be made to the system and the method used for processing of the tissue for isolating cells, for example SVF from adipose tissues, are explained with the help of figures. The figures are for the purpose of illustration only and should not be construed as limitations on the arrangement. Where ever possible referral numerals will be used to refer to the same or like parts.

Figure 1B:
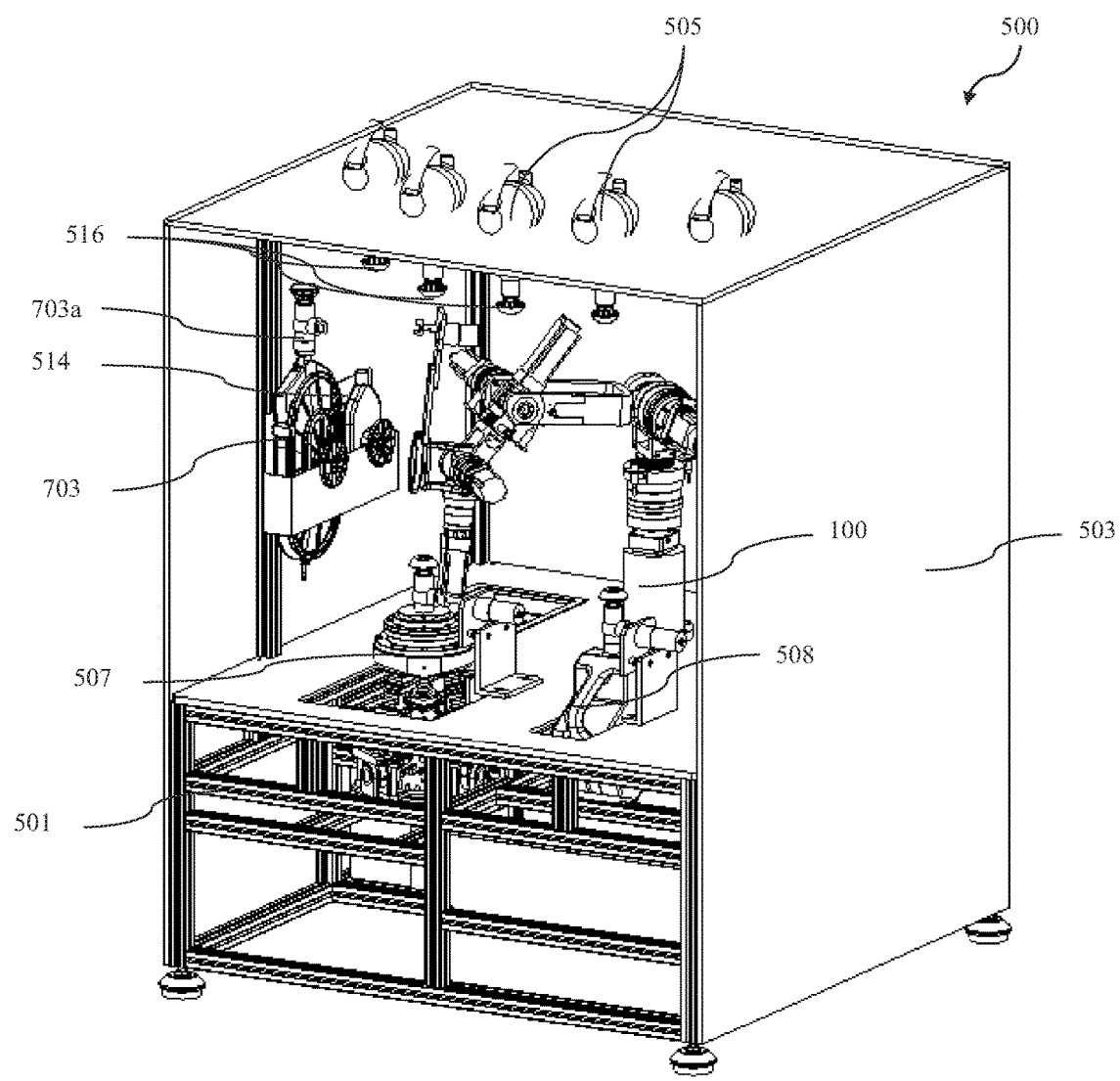

FIGS. 1a and 1b are exemplary embodiments of the present disclosure which illustrates front view and perspective views of an automated system (500) for isolating cells from tissues. The system (500) comprises a base frame (501) for supporting all components of the system (500), and enclosure (503) also called as housing mounted above the base frame (501). The enclosure is configured to support/accommodate all the components of the system (500) including storage containers (505), robotic assembly (100), the tissue processing container (703), cell concentration unit (507), and waste collection unit (508) of the system (500). In an embodiment of the disclosure, enclosure is provided such that the system (500) is hermetically sealed in the enclosure, and the enclosure (503) can be transparent or opaque. In an embodiment of the disclosure, the geometry of the enclosure (503) can vary but is not limited to cubical, square, rectangular, cylindrical and other known geometry which can be used for the purpose.

As shown in the FIG. 1a the plurality of storage containers (505a, 505b, 505c, 505d, 505e, 505f . . . 505n) [collectively referred as 505] of predetermined shape for storing liquids such as tissue samples, buffer solutions, enzymes and any other reagent are provided in the system (500). In an optional embodiment of the disclosure, the tissue is directly supplied to a tissue processing (703) container by connecting a tube between the tissue processing container (703) and a tissue harvest canister (not shown). The term tissue harvest canister referred herein above and below is a device used for collecting tissue samples from a patient. In an embodiment, the plurality of storage containers (505) is mounted on top of the enclosure or within the enclosure. However, one should note that the containers (505) can be mounted in a place inside the enclosure (503) without departing from scope of the present disclosure. In an embodiment of the disclosure, the plurality of storage containers (505) having a shape including but not limiting to circular shape, rectangular shape, square shape, toroid shape, and ellipsoidal shape. In an embodiment of the disclosure, the plurality of containers (505) is made without any sharp edges or boundaries for example in an ellipsoidal shape. The sharp boundaries in containers tends to create a sticking zone or fluid retaining zones inside the container i.e. when the fluid to be stored enters the storage containers the fluid particles tend to be retained at the sharp boundaries in the storage containers and hence complete evacuation of the fluid particles is not possible. Thus, in order to avoid this problem, the plurality of storage containers (505) are configured in ellipsoidal shape which has no sticking zone or fluid retaining zones, in summary no sharp boundaries. Thus, this type of storage containers (505) would allow complete evacuation of the fluid. This would result in avoiding tissue sticking inside the storage container (505) and enables the complete flow of tissue stored in the container to the tissue processing container (703). Further, a tissue processing container (703) also termed as washing/digestion chamber of predetermined shape is provided in the system (500) for processing the tissue samples. The tissue processing container (703) is coupled with a robotic assembly (100) which is provided in the system (500), and the robotic assembly (100) makes multi-plane movement of the tissue processing container (703). The robotic assembly (100) moves the tissue processing container (703) in pre-defined planes to perform the washing process, digestion process, and phase separation process and its combination thereof for processing the tissue to separate aqueous fraction and the fatty fraction of the digested tissue. In an embodiment of the disclosure, the phase separation step referred herein above and below is carried out while processing of adipose tissue. In an embodiment of the present disclosure, the tissue processing container (703) is designed with common inlet and outlet port (703a) for loading and unloading of fluids into the tissue processing container (703). In alternative embodiment, the tissue processing container (703) may be equipped with two ports, wherein one port is for loading of fluids and other port is for unloading of fluids.

Figure 2:
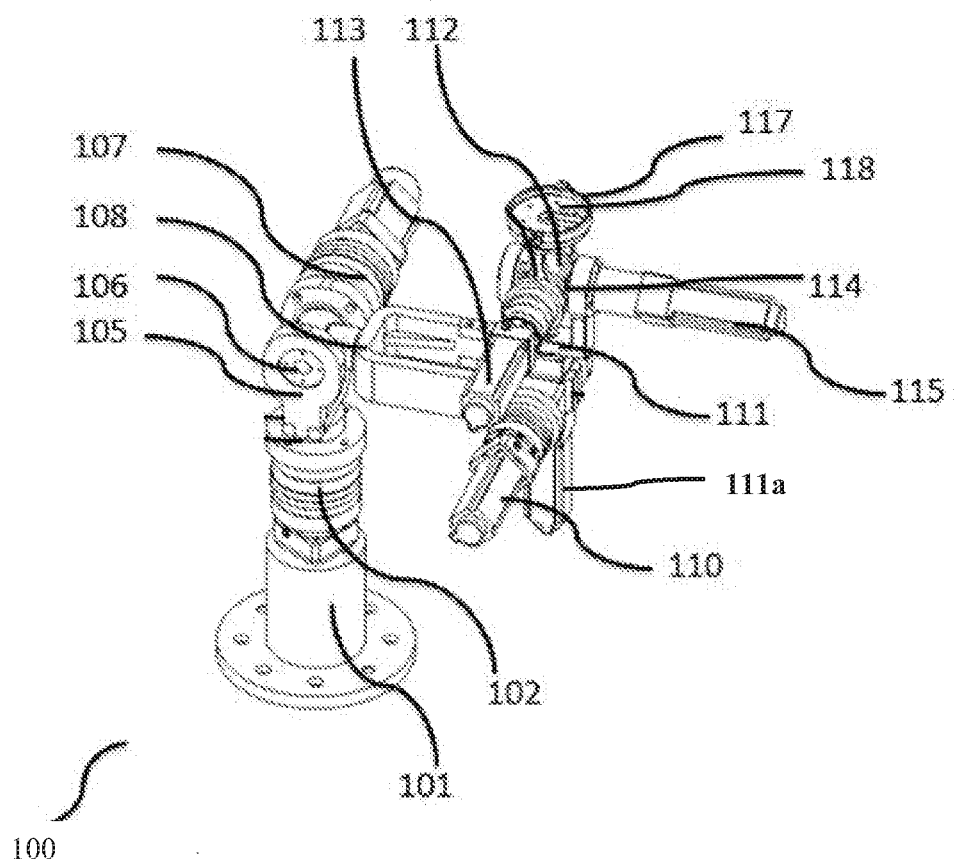
FIGS. 2 and 3 illustrates a robotic assembly of an automated system for isolating cells from tissue of the present disclosure.
Figure 3:
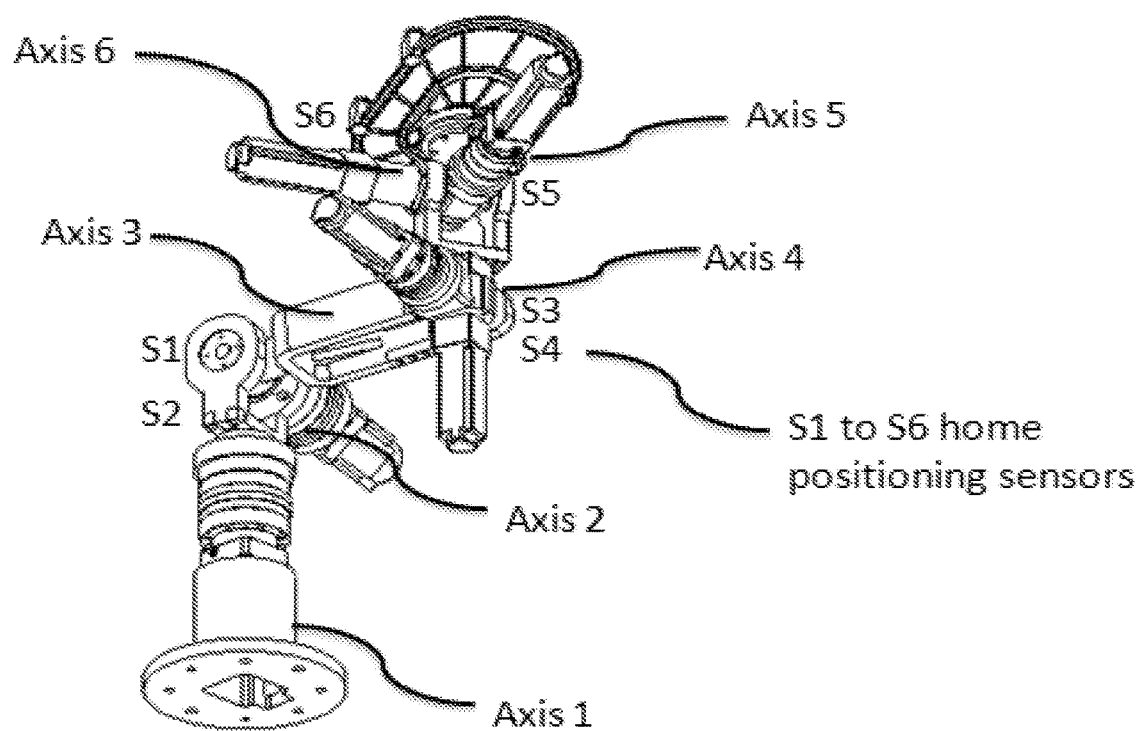

The robotic assembly (100) used in the system (500) is illustrated in the FIGS. 2 and 3. In an embodiment of the disclosure, the robotic assembly (100) is configured with 6 degrees of freedom, to move/rotate the tissue processing container (703) in predefined path to process the tissue. The six degrees of freedom refers to the freedom of movement of a rigid body in three-dimensional space. Specifically, the body is free to move forward/backward, up/down, left/right (translation in three perpendicular axes) combined with rotation about three perpendicular axes, often termed pitch, yaw, and roll.

The robotic assembly (100) comprises a base arm (101) which is mounted to a base frame (501) of the system (500) [Best shown in FIG. 1] as a first arm for the robotics assembly (100). A first motor (102) is attached at the top end of the base arm (101) to generate $1^{st}$ degree of freedom around Y axis (axis 1). The first motor (102) is coupled to a first "Y" shaped fork (105), wherein the first "Y" shaped fork (105) is configured to make 360 degree rotation along the Y axis. The first "Y" shaped fork (105) comprises a provision to accommodate a second "Y" shaped fork (108) also referred as shoulder arm. A second motor (107) is attached perpendicular to the base arm (101), at the connecting junction of the second "Y" shaped fork (108) also referred as shoulder arm with the first "Y" shaped fork (102) to generate $2^{nd}$ degree of freedom around X axis (Axis 2). The second motor (107) is configured to rotate the shoulder arm (108) up to predetermined angle i.e. 0-180 degrees with respect to X axis. Further, a third "Y" shaped fork (111) also referred as wrist link is coupled at the end of the shoulder arm (108). The wrist link (111) is sandwiched to a third motor (110) to generate $3^{rd}$ degree of motion around Z axis (Axis 3). Across the wrist link (111) a fourth motor (111a) is attached to generate $4^{th}$ degree of motion along XY plane (Axis 4). After the wrist link (111) an agitation cross link (112) is provided, to which a first and second cross link motors (113 and 115) are connected to achieve multiple sequence of multi planar motion to achieve $5^{th}$ and $6^{th}$ degrees of motion along XZ and YZ plane (Axis 5 and Axis 6).

Figure 8:
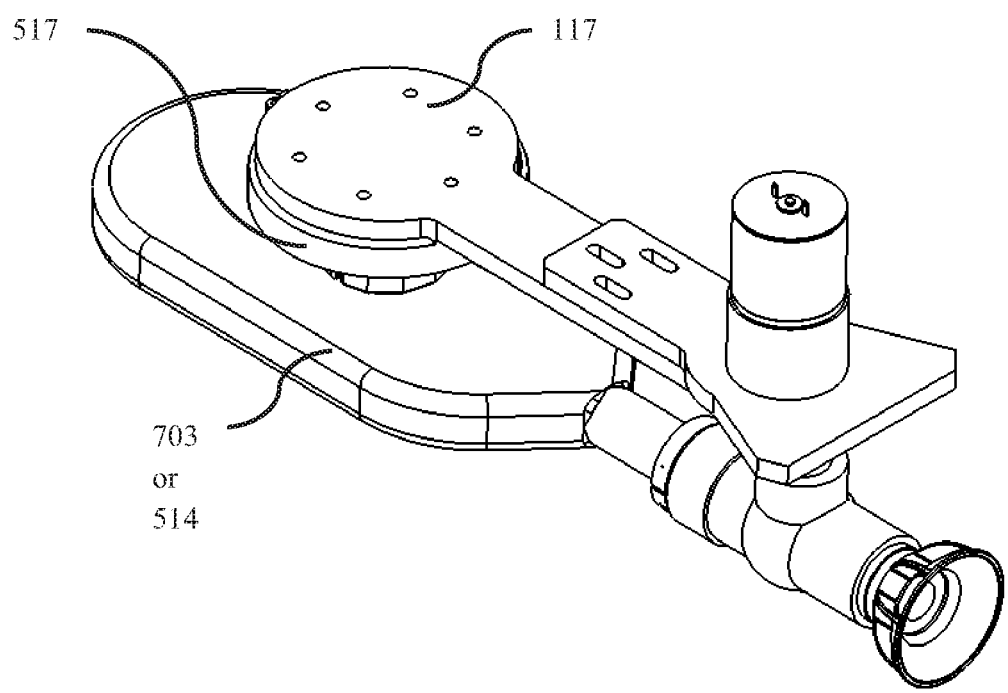
FIG. 8 illustrates perspective view of the robotic arm with a gripper for holding the tissue processing container.

In an embodiment, a container holder (117) of predetermined shape and configuration is provided on the agitation cross link (112) to hold the tissue processing container (703) of various capacity. Further, a tissue processing container (703) of predetermined shape is detachably mounted on the container holder (117) for receiving, holding and mixing of cells, tissues or liquids of different densities. The container holder (117) comprises a central recess portion (118) to receive a projecting pin of the container (703), and plurality ribs (not shown) of predefined configuration is provided in the container holder (117) to grip the surface of the container (703) firmly, thereby eliminating any loose movement of the container (703). In an embodiment of the present disclosure, gripper (517) [shown in FIG. 8] is mounted in the arm to firmly hold tissue processing container (703) through a specially designed holder frame through set of sleeve locks [not shown].

In an embodiment of the present disclosure, the motors (102, 107, 110, 111a, 113 and 115) used are type of rotary actuators such as but not limiting to servo motors, and gearbox is integrated with the said motor. The arms of robotic assembly are attached to these. In an embodiment, planetary gearboxes are used in the robotic assembly (100) for driving the robotic arms. These planetary gearboxes are highly reliable for longer use. However, other types gearboxes can be used for example harmonic gearboxes which reduce the size and increase the toque requirement in the robotic assembly (100). Further, a counter weight (701) [FIG. 7] is provided in predetermined location of the robotic assembly (100) to balance forces of movement across multiple axes.

Figure 4:
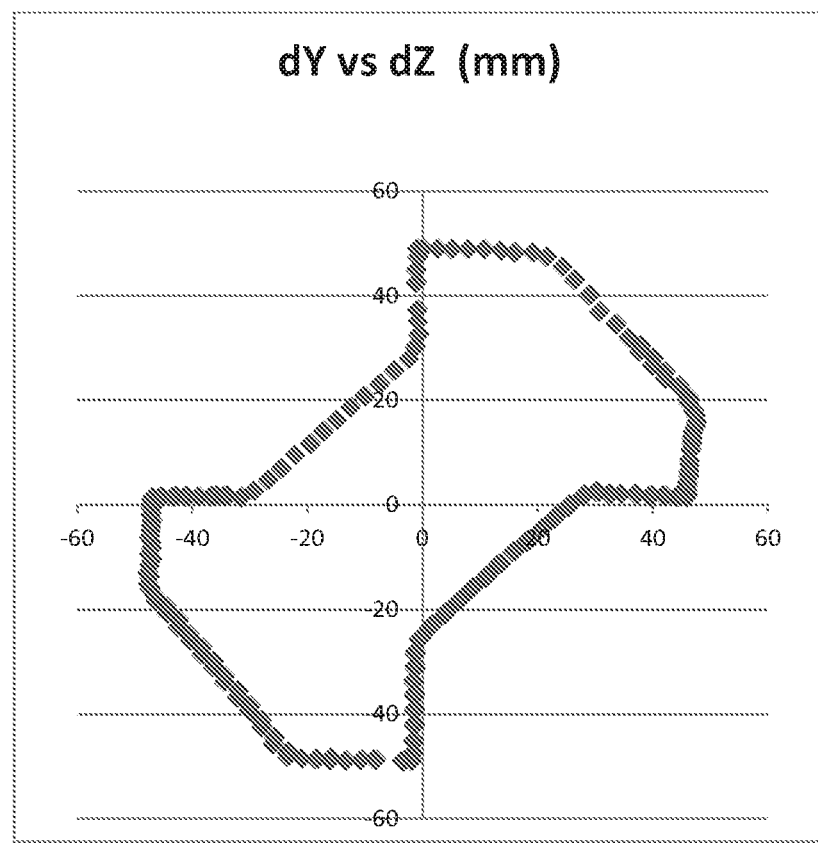
FIG. 4 illustrates a graphical representation of a path generated by the robotic assembly.

Further, as shown in the FIG. 3 at least one position sensors (S1, S2, S3, S4, S5, S6 . . . Sn) [collectively referred as S] are provided at junction of each motor (102, 107, 110, 111a, 113 and 115) of the robotic assembly (100) for sensing the home position also referred as initial position of the robotic assembly (100). The position sensors (S) are interfaced with a control unit (511), wherein said control unit (511) controls the movement of the robotic assembly (100) in a predefined path [best shown in FIG. 4] for making the multi-planar motion of the tissue processing container (703). The term multi-planar motion refereed herein above and below is defined as combination movement of the robotic arm along with the tissue processing container (703) along with all 6 degrees motion. The control unit (511) is interfaced with the motors (102, 107, 110, 111a, 113 and 115) and said control unit (511) controls the motors (102, 107, 110, 111a, 113 and 115) by varying the electrical pulse signal to motors (102, 107, 110, 111a, 113 and 115) based on the robotic movement operations stored in the control unit (511). The position sensors (S) help to move the robotic assembly (100) precisely from the starting point to the end point. A necessary electrical wiring is provided and interfaced with electrical power management system. In an embodiment of the disclosure, the position sensors (S) include proximity sensors, and the like.

As shown in FIG. 1b outlet port (516) of each of the plurality of containers (505), and the port (703a) of the tissue processing container (703) are equipped with a valve assembly (515) to facilitate the flow of fluid from each of the plurality of containers (505) to the tissue processing containers (703). In an embodiment of the disclosure, the valve assemblies are operated by actuators such as but not limiting to motor (not shown). The motors will be interfaced with the control unit (511), wherein the control unit operates the motors for opening and closing the valve assemblies to regulate the flow of liquid. The robotic assembly (100) is also configured to carry the tissue processing container (703) to the storage containers (505), and align the valve assembly in the tissue processing container (703) with the valve assembly (515) in the corresponding storage container (505) for collecting the liquids stored in the storage containers (505). When the valve assembly (515) in the tissue processing container (703) aligns with the valve assembly (515) in the storage containers (505) positional sensors [not shown] provided in the valve assemblies notifies the controller to operate the valve assemblies (515) for transferring the fluid. This would result in transfer of liquid from storage container (505) to the tissue processing container (703) through gravity and without using any fluid carrying mediums such as tubes. The elimination of tubes also results in elimination of pumps used for supply of liquid from storage container (505) to the tissue processing containers (703). The elimination of pumps and transfer of liquids using gravity eliminates the pressure imparted on the liquid such as tissues, thereby reduces damage to the cells. This in turn improves the yield and efficiency of the process.

Referring back to FIGS. 1a and 1b, the system (500) further includes a cell concentration unit (507) for filtering the aqueous fraction of tissue received from the tissue processing container (703). The robotic assembly (100) carries the tissue processing container (703) to an inlet of the cell concentration unit (507), and connects the same with the inlet valve of the cell concentration unit (507) for transferring the aqueous fraction of the tissue. In an embodiment of the disclosure, the inlet valve of the cell concentration unit (507) is provisioned with the valve assembly (515). Further, the cell concentration unit (507) is at least one of the filter assembly and the centrifugation assembly. As an example the cell concentration unit (507) is a filtration unit/assembly including plurality of filter chambers of predetermined shape fluidly connected to each other. And a filtration assistance mechanism connected to the filtration assembly. The filtration assembly is also optionally provided with a waste chamber attached to the filter chambers [not shown] for collecting remaining portion of aqueous fraction of the tissues after the filtration. The filtration can be performed by techniques such as but not limiting to simple filtration, pressure assisted filtration, vacuum assisted filtration, and vibration assisted filtration or any combination thereof. Further, a waste collection unit (508) is provided in the system (500), and said waste collection unit (508) is configured to receive waste fraction of tissues from the cell concentration unit (507), and the tissue processing container (703). In an embodiment of the disclosure, the waste collection unit (508) is equipped with the valve assembly (515) one which is similar to the valve assembly (515) provided in each of the plurality of containers (505).

The system (500) comprises one or more disposable elements such as storage containers (505), tissue processing container (703), filter elements, waste collection unit (508). All the disposable elements used in the system (500) are made of medical grade material suitable for processing biological samples meant for clinical use. All the disposable elements are sterilized by γ-irradiation or any other means known in the art, and are intended for single/one time use only, and supplied with the system (500) as a sterile package. In another embodiment the sterile package may be interlocked with the system (500) using RFID tags. In one embodiment of the disclosure, the control unit (511) is mounted on top surface of the enclosure (503) and the control unit (511) is provided with an user interface (506) having a display and input buttons to feed-in required parameters for processing the tissues.

Referring to FIG. 1b, the system (500) comprises a wash container (514) inside the enclosure (503). The wash container (514) is provided in a hand change station (not numbered) inside the enclosure (503). In an embodiment of the disclosure, the wash container (514) is of similar shape of the tissue processing container (703), or may have any other shape which serves the purpose. The wash container (514) is provisioned in the system (500) as an optional embodiment to receive wash buffer solution from the storage container (505) and supply the same to the cell concentration unit (507) for isolating the cells. After the supply of processed tissue from tissue processing container (703) to the cell concentration unit (507), the robotic assembly (100) discards the tissue processing container (703) in the discard station (not shown), and then a new gripper (517) is attached to the container holding arm (117). Then, the robotic assembly (100) picks up the wash container (514) from the hand change station, and move in pre-programmed path to execute subsequent operations. In one embodiment, the pre-programmed path is stored in the control unit (511).

Figure 5:
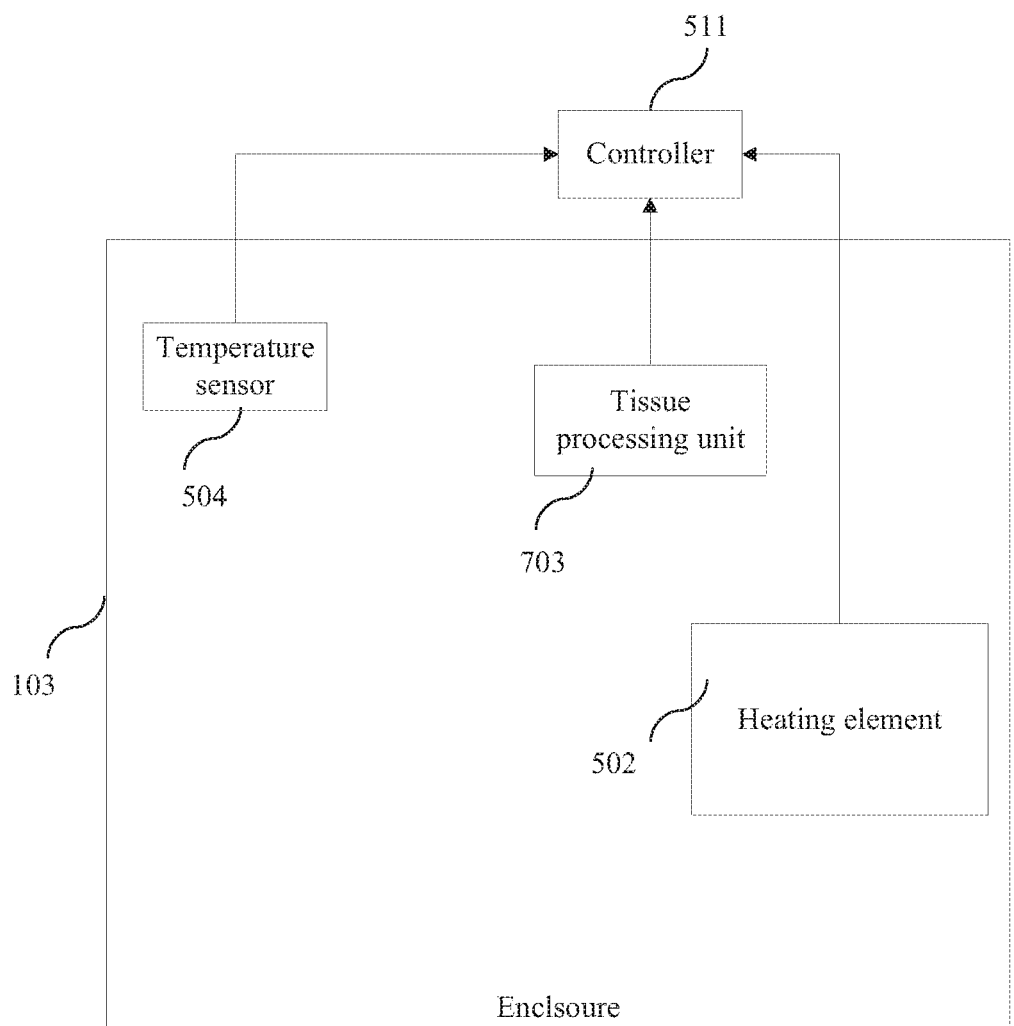
FIG. 5 illustrates block diagram of an automated system for isolating cells from tissue of the present disclosure.

In an embodiment of the present disclosure, the system (500) comprises at least one temperature sensor (504) [best shown in FIG. 5] placed in the enclosure (503) to measure and regulate the temperature inside the enclosure (503). The temperature sensor (504) is interfaced with the control unit (511) to maintain the temperature of the enclosure (503) within a predetermined limit. The temperature inside the enclosure (503) is maintained in a range from about 35° C. to about 38° C. preferably from about 36.5° C. to about 37.5° C. In an embodiment of the present disclosure, a heating element (502) is provided in a predetermined location of system (500) for heating the tissue processing container (703) when it is required during the process, and the heating element (502) also dissipates heat inside the enclosure (503) when the temperature inside the enclosure (503) falls below the predetermined limit. The heating element (502) is interfaced with the control unit (511), and said control unit (511) regulates the operation of the heating element (502) for maintaining predetermined temperature inside the enclosure (503) as required for the tissue digestion process. In an embodiment of the disclosure, heating element (502) is moulded ceramic, however, other type of conventionally known heaters can also be used depending upon the heat load.

In another embodiment of the present disclosure, the temperature inside the enclosure can be maintained by a method selected from a group comprising but not limited to warm air circulation, or use of infrared heating mechanism such as radiation, convention or other such technology known in the art.

In an embodiment of the present disclosure, the storage containers (505) and the tissue processing container (703) may be provided with Radio Frequency Identification (RFID) tags. The RFID tags are interfaced with a control unit (511), wherein the control unit (511) stores the data about the position of each of the storage container (511) in the system (500) using RFID tags of the corresponding storage container (505). Further, the control unit (511) operates the robotic assembly (100) to move to a particular position of the storage container (505) based on the data received from the RFID tag. Also, the RFID signals will be stored in a data logger. The system (500) will be interfaced with an architecture for remote monitoring of an automated system [best shown in FIG. 6], which comprises a processor which continually tracks all signals with a time stamp and stores the data to a memory. This data is transferred to a central server at predefined intervals through the internet. The server will have an application layer which will ensure that data from each unit operating in the field is archived appropriately and processed for a specific dashboard. An application running in the back end will generate early warning for any deviation in the functioning of the system (500). Information delivered through SMS may enable service personnel to proactively interact with customers. The service architecture is used to assist customers as and when the need arises while processing a sample or for routine upkeep for reliable performance.

Figure 7:
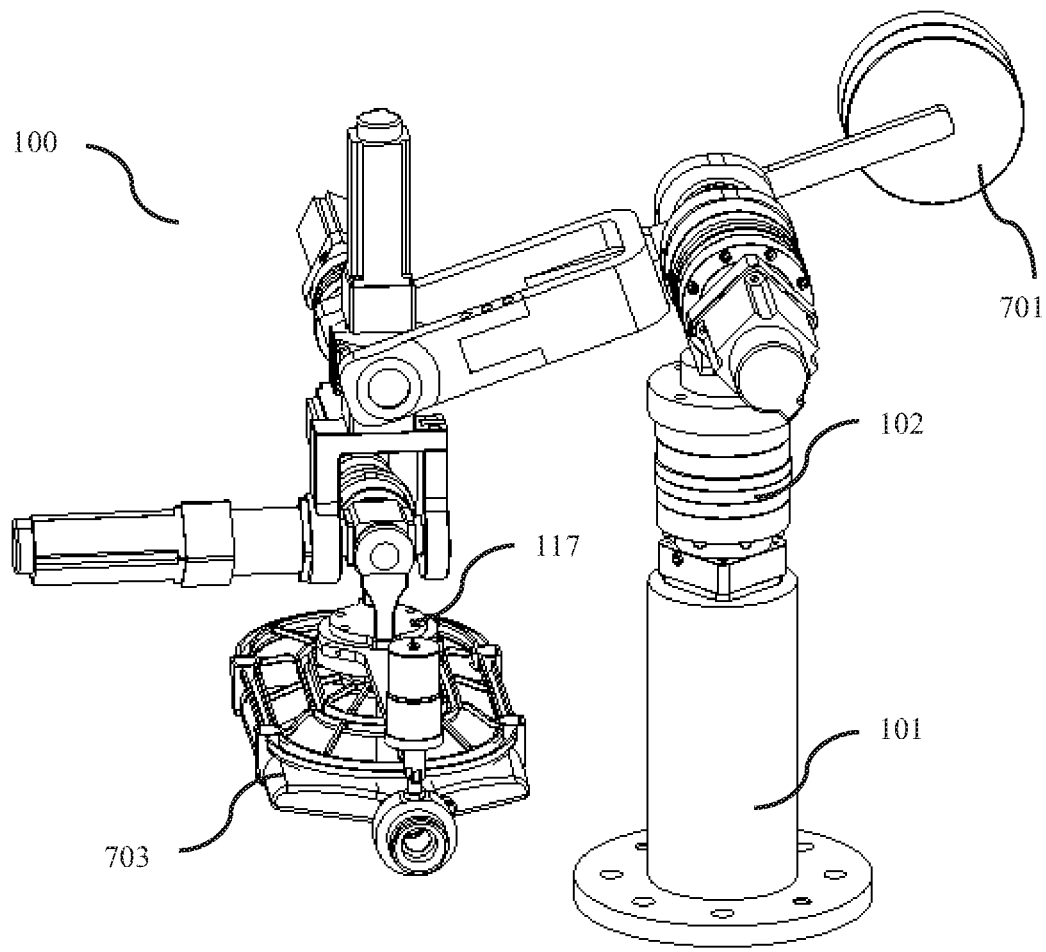
FIG. 7 illustrates a robotic assembly of an automated system for isolating cells from tissue of the present disclosure with tissue processing container.

FIG. 7 is an exemplary embodiment of the present disclosure which illustrates a robotic assembly (100) with the tissue processing container (703). The tissue processing container (703) is detachably mounted on container holder (117) of the robotic assembly (100). The container holder (117) comprises a central recess portion (118) to receive a projecting pin of the tissue processing container (703), and plurality of ribs of predefined configuration is provided in the container holder (117) to firmly grip the surface of the tissue processing container (703), thereby eliminating any loose movement of the tissue processing container (703). In an embodiment of the present disclosure, at least one wash container (514) is provided in hand change station of the system (500) [FIG. 1]. The wash container (514) is configured in a different dimension/same dimension as tissue processing container (703), and is adapted to be detachably fixed to the container holder (117) of the robotic assembly (100). The wash container (514) may be used for additional processes such as but not limiting to washing or different type of digestion to achieve specific goal. During washing process the robotic assembly (100) is configured to discard the gripper of the tissue processing container (703) in discard station, and pick up the a new gripper automatically from the hand change station. Once new gripper is attached to the container holding arm (117), the robotic assembly (100) picks up the wash container (514) from the hand change station, and move in pre-programmed path to execute subsequent operations. In one embodiment of the present disclosure, the wash container (514) may be filled with wash buffer solution, which is then supplied to the cell concentration unit (507) for washing the SVF concentrate by filtration. The wash buffer can be supplied into any one of the chambers of the cell concentration unit (507), preferably into the final chamber containing SVF concentrate.

Figure 9A:
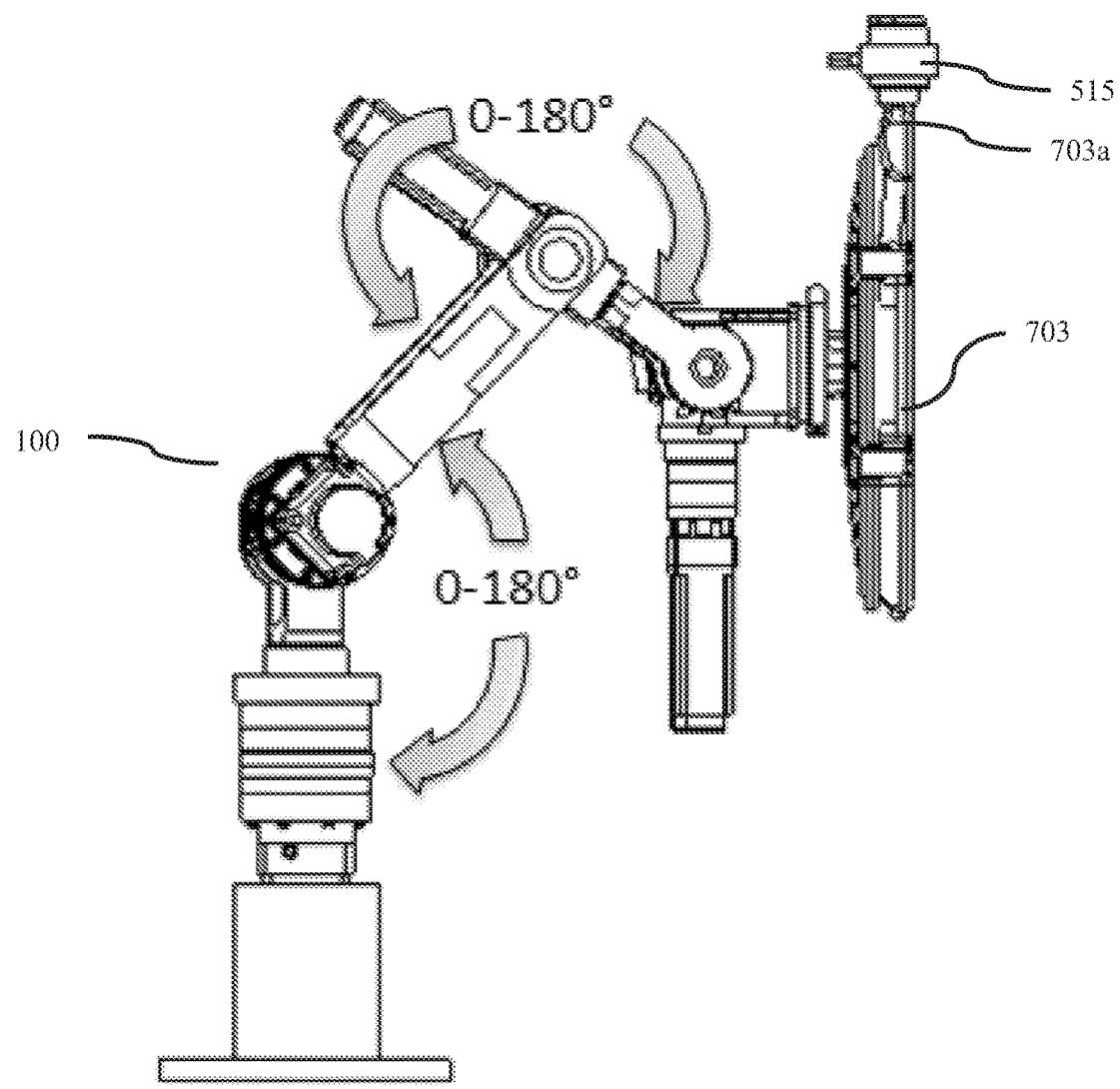
FIGS. 9a and 9b illustrates position of the robotic arm and the tissue processing container during loading and unloading conditions respectively.
Figure 9B:
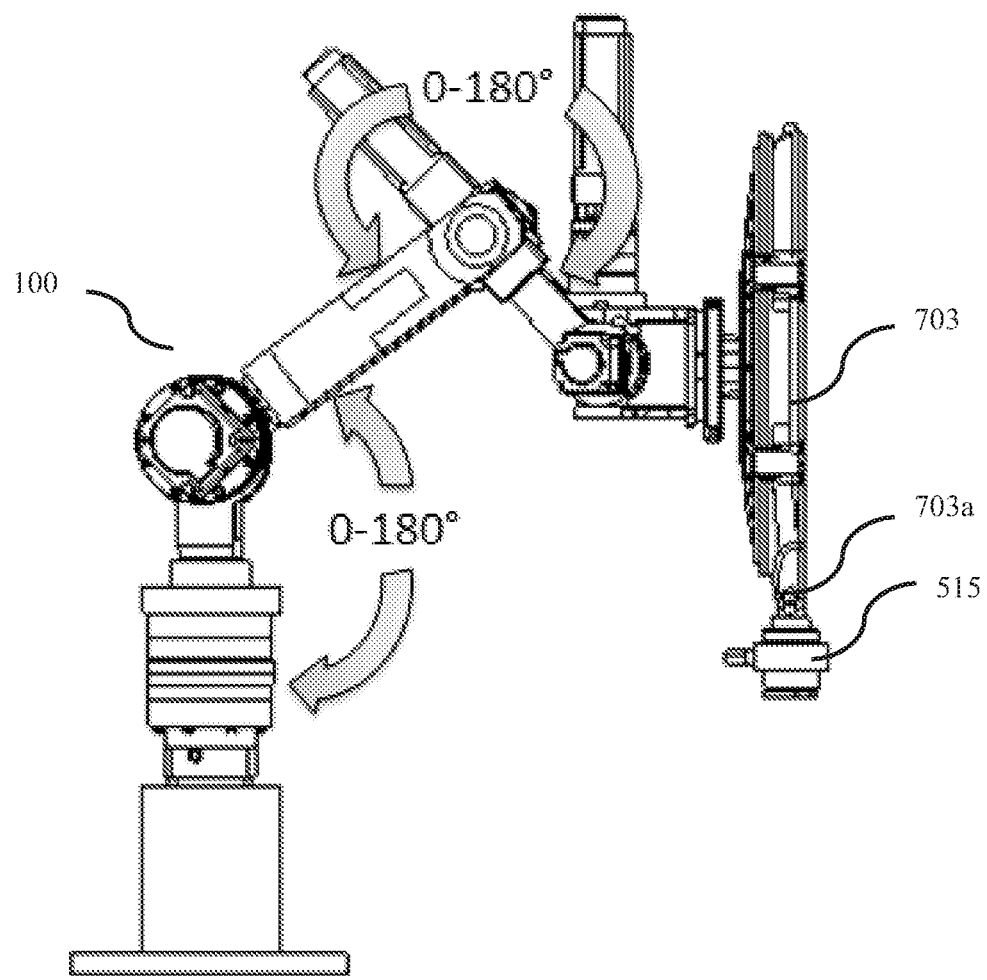

FIGS. 9a and 9b are exemplary embodiments of the present disclosure illustrating the position of the robotic arm of the robotic assembly (100) and the tissue processing container (703) during loading and unloading condition respectively. In the loading condition, the robotic assembly (100) carries the tissue processing container (703) toward each of the plurality of the containers (505), and aligns the valve assembly (515) provided in port (703a) of the tissue processing container (703) with the valve assembly (515) of the corresponding container (505) for loading. During loading of fluids from the plurality containers (505) to the tissue processing container (703) it is held in upright position as shown in FIG. 9a. Once, the valve assemblies (515) are aligned the control unit (511) will operate the valve assemblies to allow the flow of fluid from the storage containers (505) to the tissue processing container (703) due to action of gravity. During, the loading condition the robotic assembly (100) carries the tissue processing container (703) toward at least one of the waste collection unit (508) and the cell concentration unit (507), and aligns the valve assembly (515) provided in port (703a) of the tissue processing container (703) with the valve assembly (515) of waste collection unit (508) and the cell concentration unit (507) for unloading of the processed tissues form the tissue processing container (703). During un-loading of fluids from the tissue processing container (703) it is held in inverted position as shown in FIG. 9b. Once, the valve assemblies (515) are aligned the control unit (511) operates the valve assemblies to allow the flow of fluid from the tissue processing container (703) to waste collection unit (508) or cell concentration unit (507) due to action of gravity.

In an embodiment of the disclosure, the control unit (511) may be implemented in system (500), or in a computing unit which is interfaced with the system (500). The control unit (511) may also be termed as a processing unit. The processing unit may comprise at least one data processor for executing program components for executing user- or system-generated requests. The processor may include specialized processing units such as integrated system (bus) controllers, memory management control units, floating point units, graphics processing units, digital signal processing units, etc. The processing unit a may include a microprocessor, such as AMD Athlon, Duron or Opteron, ARM's application, embedded or secure processors, IBM PowerPC, Intel's Core, Itanium, Xeon, Celeron or other line of processors, etc. The processing unit may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Figure 6:
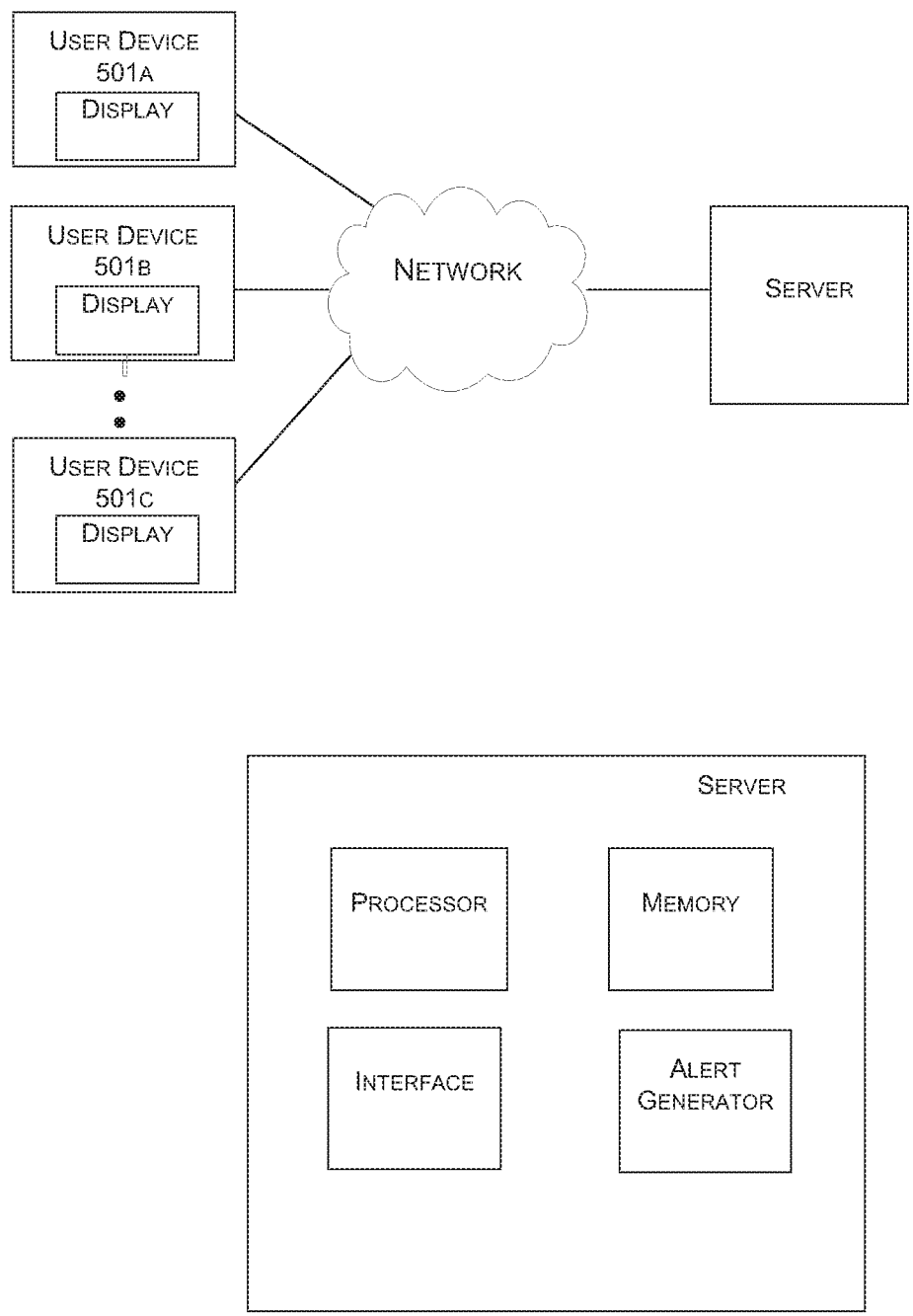
FIG. 6 illustrates block diagram of an exemplary architecture for remote monitoring of an automated system for isolating cells from tissue of the present disclosure.

In some embodiments, the server [shown in FIG. 6] may comprise a central processing unit ("CPU" or "processor"). The processor may comprise at least one data processor for executing program components for executing user- or system-generated business processes. A user may include a person, a person using a device such as those included in this disclosure, or such a device itself. The processor may include specialized processing units such as integrated system (bus) controllers, memory management control units, floating point units, graphics processing units, digital signal processing units, etc. The processor may be disposed in communication with one or more input/output (I/O) devices (not shown). The I/O interface may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc. Using the I/O interface, the computer system may communicate with one or more I/O devices (not shown). For example, the input device may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output device may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc. In some embodiments, the processor may be disposed in communication with a memory 705 (e.g., RAM, ROM, etc. not shown in FIG. 6). The memory may include, without limitation, memory drives, removable disc drives, etc., employing connection protocols such as serial advanced technology attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

In a preferred embodiment of the present disclosure, the stromal vascular fraction is obtained by following the process steps as mentioned below—
 a. a predetermined quantity of a tissue sample (e.g. fat tissue) is supplied to a tissue processing container by connecting the tissue processing container valve to the valve of the tissue storage containers. In an optional embodiment of the disclosure, the tissue is supplied to a tissue processing container by connecting a tube between the tissue processing container and a tissue harvest canister.

b. then wash buffer solution contained in storage containers is supplied to a tissue processing container by connecting the tissue processing container valve to the valve of the wash buffer solution storage container.
c. tissue samples are washed with wash buffer solution by agitating the mixture in the tissue processing container with the help of robotic assembly, wherein the robotic assembly moves the tissue processing container in predefined path.
d. the mixture is separated into initial fatty upper fraction and a aqueous lower fraction in the tissue processing container by allowing phase separation of the mixture; the phase separation is carried out by tilting the digestion chamber 90 degrees with respect to X axis by a robotic assembly.
e. the initial aqueous fraction obtained in previous step is disposed to a waste collection unit; the steps b-e are repeated for about 1-6 preferably 3-4 times.
f. a predetermined quantity of a digestive buffer contained in a digestive buffer container is passed into the tissue processing container by connecting the tissue processing container valve to the digestive buffer container valve.
g. the initial fatty upper fraction is mixed with the digestive buffer by agitating the mixture in the tissue processing container for a predetermined time to carry out the digestion process. During digestion process a predefined temperature is maintained in the enclosure with the help of heating element and temperature sensors interfaced with the control unit;
h. the mixture is separated in to a—final fatty upper fraction and a aqueous lower fraction containing SVF by allowing phase separation of the mixture in the tissue processing container;
i. the final aqueous lower fraction obtained in the previous step is directed to a cell concentration unit, wherein the robotic assembly carries the tissue processing container and supplies the final aqueous lower fraction to the cell concentration unit; the tissue processing container valve is connected to the valve of the cell concentration unit for supplying final aqueous lower fraction. and
j. filtering the final aqueous fraction within the cell concentration unit, comprising of filtration assembly, optionally along with removal of red blood cells to concentrate the final aqueous fraction containing said SVF cells.

The SVF concentrate is then washed with wash buffer solution in order to remove the digestive enzyme from the final SVF cell suspension. The SVF wash is performed as follows:

Option 1:
a. The final fatty fraction in the tissue processing container is disposed to the waste collection unit.
b. The tissue processing container is then filled with a predetermined quantity of wash buffer solution and optionally rinsed by agitation to remove residual tissue and enzyme, and the wash buffer is disposed to the waste collection unit.
c. The rinsed tissue processing container is again filled with wash buffer solution, which is then supplied to the cell concentration unit for washing the SVF concentrate by filtration (The wash buffer can be supplied into any one of the chambers of the filtration unit. Preferably supplied directly into the final chamber containing SVF concentrate).
d. Step c can be performed once or multiple times to completely remove the digestive enzyme to obtain the final SVF output.

Option 2:
a. The tissue processing container is discarded by the robotic arm at a discard station.
b. A wash container is picked up by the robotic arm from the hand change station. The wash container can be a tissue processing container or a container of any other shape and size.
c. The wash container will be filled with wash buffer solution, which is then supplied to the cell concentration unit for washing the SVF concentrate by filtration (The wash buffer can be supplied into any one of the chambers of the filtration unit. Preferably supplied directly into the final chamber containing SVF concentrate).
d. Step c can be performed once or multiple times to completely remove the digestive enzyme to obtain the final SVF output.

Advantages of the Robotics Enabled System Described in the Present Disclosure as Compared to Conventional Systems:

1. Tubeless system: The robotics enabled system described in the present disclosure operates without the use of tubes. A tubeless system provides the following advantages:
   a) Assured Sterility: Manual connection is a risk factor that can compromise the sterility or aseptic nature of the cell isolation system Improper handling can introduce microbial contamination or a breach in the closed nature of the cell isolation system. The present tubeless system enabled with robotics and synchronized valves ensures a closed aseptic flow-path that eliminates the chance of microbial contamination.
   b) Eliminates manual errors arising from incorrect connection: Minimal human intervention. The robotics enabled system operates with minimal manual intervention, which decreases the probability of errors and chances of contamination.
   c) Since the tubeless system does not employ pumps, the SVF/cells are not subjected to pressure stress and resulting damages.
2. Increased precision: Increased precision obtained with the robotics enabled system leads to superior consistency and reliability in performance
3. Flexibility—Process changes however minor or major can be easily introduced through changes in software/algorithm. Additional changes in hardware/construction and investment in the same are not required. Process changes can include, but are not limited to, the following:
   a) Different process for different biological tissues can be handled by the same hardware, with different software inputs;
   b) Future improvements in the existing process such as path and speed of agitation etc. to obtain improved yield/viability of the end product; and
   c) Future modifications in the existing process to obtain a different cell population from the same tissue.

EQUIVALENTS

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 500 | System for processing of tissue |
| 501 | Base of system |
| 502 | Heating element |
| 503 | Enclosure |
| 505a-505f | Storage container |
| 506 | Display monitor |
| 507 | Cell concentration unit |
| 508 | Waste collection unit |
| 511 | Control unit |
| 512 | RFID connection module |
| 513 | Caster wheel |
| 514 | Wash container |
| 515 | Valve assembly |
| 516 | Outlet port of the storage containers |
| 517 | Gripper |
| 703 | Tissue processing container |
| 703a | Port of the tissue processing container |
| 701 | Counter weight |
| 100 | Robotic assembly |
| 101 | Base of the robotic assembly |
| 102 | First motor |
| 105 | First "Y" shaped fork |
| 107 | Second motor |
| 108 | Second "Y" shaped fork |
| 110 | Third motor |
| 111 | Third "Y" shaped fork |
| 111a | Fourth motor |
| 112 | Agitation link |
| 113 and 115 | Cross link motors |
| 117 | Container holder |
| 118 | Central recess portion |
| S1-S6 | Position sensors |

We claim:

1. An automated system for processing of tissue, the system comprising:
a plurality of containers, wherein each of the plurality of containers has an outlet port and stores at least one of tissue samples, buffer solutions, enzymes and reagents;
a tissue processing container for processing of the tissue, the tissue processing container having an inlet port;
wherein the outlet port of each of the plurality of containers and the inlet port of the tissue processing container are each provided with a valve assembly;
a robotic assembly coupled to the tissue processing container, wherein the robotic assembly is configured to:
carry the tissue processing container towards each of the plurality of containers, and align the inlet port of the tissue processing container with the outlet port of each of the plurality of containers for collecting at least one of tissue samples, buffer solutions, enzymes and reagents; and
move the tissue processing container in multiple-planes to perform at least one of a washing process, digestion process, phase separation process and combination thereof for separating an aqueous fraction and a fatty fraction from digested tissue samples; and
a control unit interfaced with the robotic assembly and programmed to control the carrying and moving operations of the robotic assembly while processing the tissue.

2. The system as claimed in claim 1, wherein the tissue is mammalian tissue selected from at least one of adipose tissue, placental tissue and umbilical cord tissue.

3. The system as claimed in claim 2 isolates Stromal Vascular Fraction (SVF) cells by processing adipose tissue, and multi-potent stem/stromal cells from placental and umbilical cord tissue.

4. The system as claimed in claim 1 further comprises a cell concentration unit configured to filter the aqueous fraction of digested tissue for isolating cells, wherein the cell concentration unit receives the aqueous fraction tissue sample from the tissue processing container.

5. The system as claimed in claim 4, wherein the cell concentration unit is at least one of a filter assembly, a spinner and a centrifugation assembly.

6. The system as claimed in claim 1 comprises a waste collection unit for receiving at least one of aqueous fraction of tissues and fatty fraction of tissues from the tissue processing container.

7. The system as claimed in claim 1 is enclosed in a chamber.

8. The system as claimed in claim 1, wherein the control unit is provided with a user interface having a display unit and input buttons to feed in required parameters for processing the tissue.

9. The system as claimed in claim 1 comprises at least one temperature sensor, placed in a chamber to measure and regulate the temperature of the chamber, wherein the temperature sensor is interfaced with the control unit.

10. The system as claimed in claim 1 comprises at least one heating element placed in a chamber, wherein the heating element is interfaced with the control unit to maintain the temperature of the chamber within a predetermined limit, and heat the tissue processing container.

11. The automated system as claimed in claim 1 is used for processing of biological tissue samples.

12. The system as claimed in claim 1 wherein the valve assemblies are interfaced with the control unit.

13. The system as claimed in claim 1 comprises a wash container adapted to be coupled to the robotic assembly.

14. The system as claimed in claim 13, wherein the robotic assembly is configured to:
   carry the wash container towards the plurality of containers, and align an inlet port of the wash container with an outlet port of a container which is storing a wash buffer solution for collecting the wash buffer solution; and
   carry the wash container towards a cell concentration unit, and align the outlet port of the wash container with an inlet port of the cell concentration unit for supplying the wash buffer solution to the cell concentration unit for washing the aqueous fraction tissue sample.

15. The system as claimed in claim 1, wherein each of the plurality of containers and the tissue processing container are equipped with a radio frequency identification tags.

16. The system as claimed in claim 1, wherein the robotic assembly comprises a plurality of sensors.

17. The system as claimed in claim 16, wherein the plurality of sensors are interfaced with the control unit to control the movement of the robotic assembly in a pre-defined path.

18. A method for processing of tissue in an automated system the method comprises acts of:
   a. receiving tissue samples and wash buffer solution to a tissue processing container, wherein a robotic assembly aligns inlet ports of the tissue processing container to outlet ports of each of a plurality of containers storing tissues and wash buffer solution;
   b. washing the tissue samples with wash buffer solution by agitating a mixture in the tissue processing container with the help of the robotic assembly, wherein the robotic assembly moves the tissue processing container in multiple planes;
   c. allowing phase separation of the mixture to obtain an initial fatty upper fraction and an initial aqueous lower fraction in the tissue processing container, wherein the phase separation is carried out by tilting the tissue processing container by 90 degrees with respect to an X axis by the robotic assembly;
   d. disposing the initial lower aqueous fraction obtained in step (c) to a waste collection unit, wherein the robotic assembly aligns inlet ports of waste collection unit with an outlet port of the tissue processing container;
   e. receiving a predetermined quantity of a digestive buffer contained in a digestive buffer container to the tissue processing container, wherein the robotic assembly aligns the inlet port of the tissue processing container to an outlet port of the container storing digestive buffer solution;
   f. digesting the fatty upper fraction with the digestive buffer by agitating the mixture in the tissue processing container with the help of robotic assembly, wherein the robotic assembly moves the tissue processing container in multiple planes;
   g. allowing phase separation of the mixture in the tissue processing container to obtain a final fatty upper fraction and a final aqueous lower fraction, wherein the phase separation is carried out by tilting the tissue processing container by 90 degrees with respect to the X axis by a the robotic assembly.

19. The method as claimed in claim 18 further comprises an act of detecting a position of the robotic assembly by sensors, and regulating the robotic assembly by a control unit to carry the tissue processing container toward each of the plurality of containers and the waste collection unit.

20. The method as claimed in claim 18 further comprises an act of detecting alignment of the tissue processing container with at least one of, the plurality of containers and waste collection unit by a control unit, and operating a valve assembly.

* * * * *